United States Patent [19]

LeBlanc

[11] Patent Number: 5,029,572
[45] Date of Patent: Jul. 9, 1991

[54] BODY WARMING DEVICE

[76] Inventor: Tom LeBlanc, 2966 St. Clair Avenue East, East York, Ontario, Canada, M4B 1P1

[21] Appl. No.: 411,747

[22] Filed: Sep. 25, 1989

[51] Int. Cl.⁵ ............................................. A61F 7/00
[52] U.S. Cl. ............................. 126/204; 128/201.13; 128/204.17
[58] Field of Search ............... 128/379, 380, 401, 399, 128/400, 402, 201.21, 201.13, 204.17, 205.12; 126/204; 4/535, 536; 2/2.1, 79

[56] References Cited

U.S. PATENT DOCUMENTS

| | | | |
|---|---|---|---|
| 2,429,234 | 10/1947 | Miller | 128/379 |
| 2,460,269 | 2/1949 | Appeldoorn | 126/20 X |
| 2,551,142 | 5/1951 | Lessard | 126/204 |
| 2,648,325 | 8/1953 | Siple | 126/204 |
| 3,153,720 | 10/1964 | Petronio et al. | 2/2.1 X |
| 3,229,681 | 1/1966 | Gluckstein | 126/204 |
| 3,807,396 | 4/1974 | Fischel | 128/201.21 |
| 4,038,698 | 8/1977 | Smith | 126/204 X |
| 4,683,869 | 8/1987 | Wilcox | 126/604 |

Primary Examiner—Edgar S. Burr
Assistant Examiner—Moshe I. Cohen

[57] ABSTRACT

The present invention provides a body warming device comprising a breathing tube extending to a body fitting member to be worn under a overcoat. The body fitting member receives relatively warm air breathed into the device through the breathing tube and has numerous small exhaust ports for dispersing that warm air from the device where it is effectively trapped and provides a warming effect beneath the overcoat. The device further includes a lower end water trap where moisture condensed out of the breathed air before it leaves the device is collected, with the water trap being removable to then drain the water from the device.

4 Claims, 2 Drawing Sheets

FIG. 4.
FIG. 5.
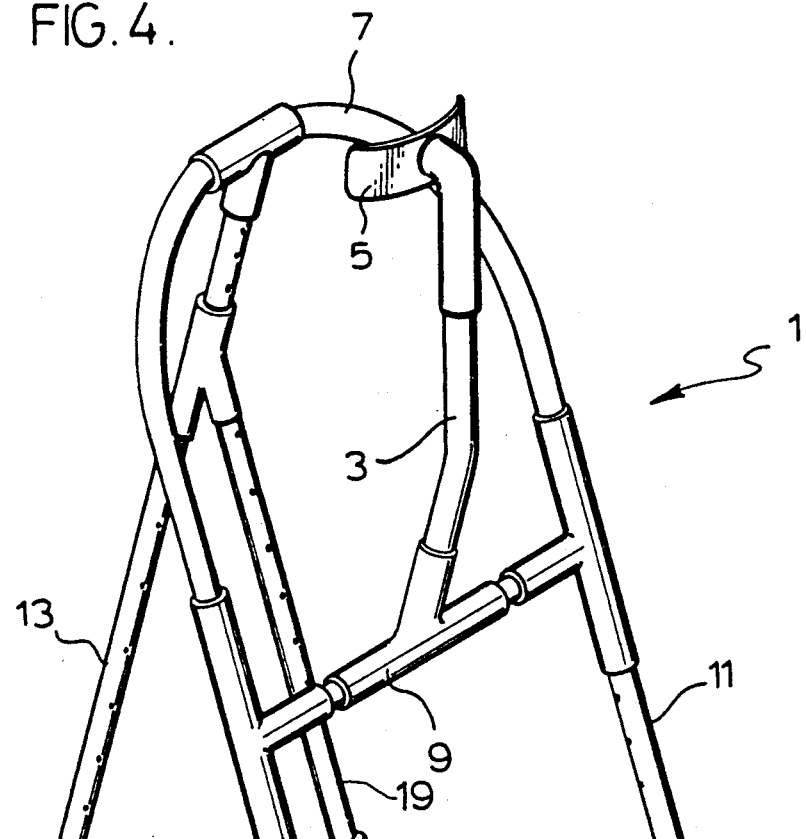
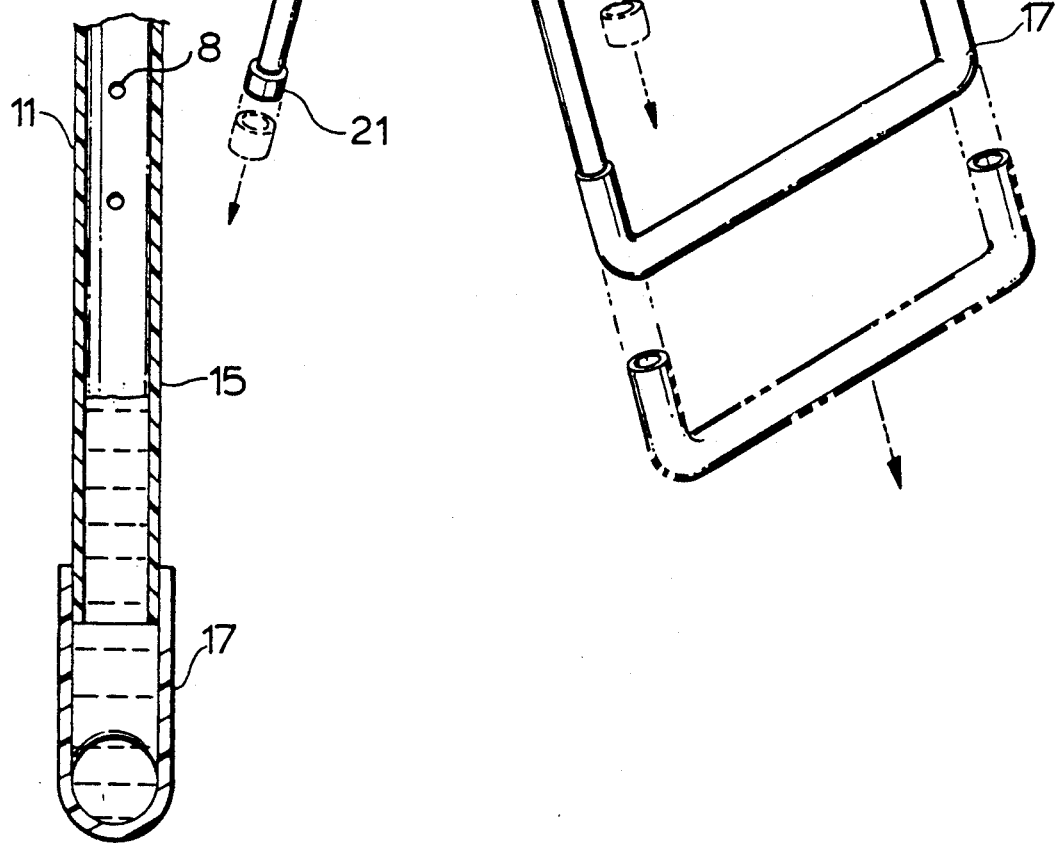

BODY WARMING DEVICE

FIELD OF THE INVENTION

The present invention relates to a body warming device which uses ones own relatively warm breath exhaled through the device beneath an overcoat or the like which is worn over the device.

BACKGROUND OF THE INVENTION

As most people will appreciate in very cold weather even the warmest of jackets may not provide sufficient insulation from the cold. Added to this is the fact that many of today's warmest coats have a nylon or nylon like inner surface which feels cold when the jacket is first put on before ones body has a chance to heat up, which either takes a very long time or may not happen at all in such very cold weather.

SUMMARY OF THE PRESENT INVENTION

The present invention provides a body warming device providing a supplementary heating effect beneath an overcoat and thereby substantially enhancing the insulating effect of the coat.

More particularly the present invention provides a body warming device comprising a breathing tube extending to a body fitting member to be worn under the overcoat with the body fitting member receiving relatively warm air breathed into the tube and having a plurality of small exhaust ports for dispersing that warm air from the device beneath the coat.

The device includes a removable lower end water trap where moisture condensed from the air breathed into the device collects and can then be removed from the device.

The device of the present invention does not rely on any outside power sources such as batteries or the like and therefore is both simple and effective.

BRIEF DISCUSSION OF THE DRAWINGS

The above as well as other advantages and features of the present invention will be described in greater detail according to the preferred embodiments of the present invention inwhich:

FIG. 4 is an enlarged perspective view of the overall preferred embodiment body warming device of FIGS. 1 and 2.

FIG. 5 is a sectional view through the lower end water trap of the device of FIG. 4.

Figure 1:
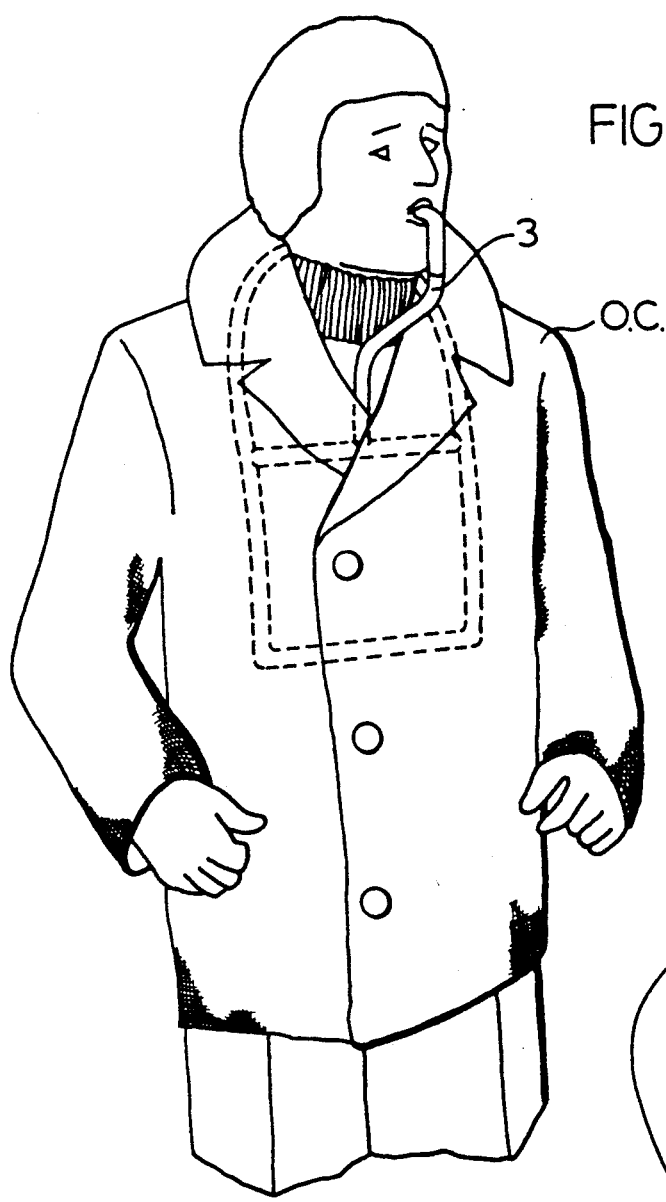
FIG. 1 shows an individual using a body warming device beneath an overcoat according to a preferred embodiment of the present invention.

DETAILED DESCRIPTION ACCORDING TO THE PREFERRED EMBODIMENTS OF THE PRESENT INVENTION:

As seen in FIG. 1 an individual wearing overcoat O.C. is breathing into a body warming device generally indicated at 1 and comprising a breathing tube 3 and a body fitting member shown in phantom lines beneath the overcoat. The overall device including both the breathing tube and the body fitting member is best seen in FIG. 4 of the drawings.

More particularly, warming device 1 comprises the breathing piece 3, the body fitting member which is indicated at 7 in FIG. 4, and a mouth fitting piece 5 on the breathing tube which substantially eases breathing into the tube. The breathing tube extends through a manifold portion 9 down to the body fitting member which in turn includes a forward chest fitting portion 11 and a rearward back fitting portion 13. Manifold 9 insures that air breathed in through breathing tube 3 branches off to both the chest and the back fitting portions of body fitting member 7.

Figure 3:
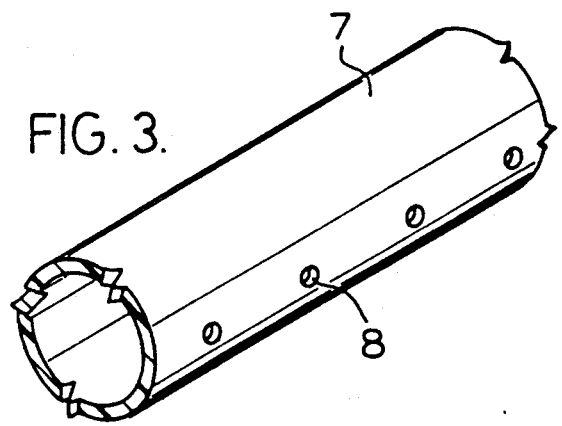
FIG. 3 is an enlarged view of a short section of tube from the body warming device of FIGS. 1 and 2.

FIG. 3 shows how body fitting member 7 is provided with a series of small holes 8 which can also be seen in FIG. 4 over the length of both the chest and back fitting portions. These holes provide exhaust ports for the relatively warm air breath in through tube 3.

Figure 2:
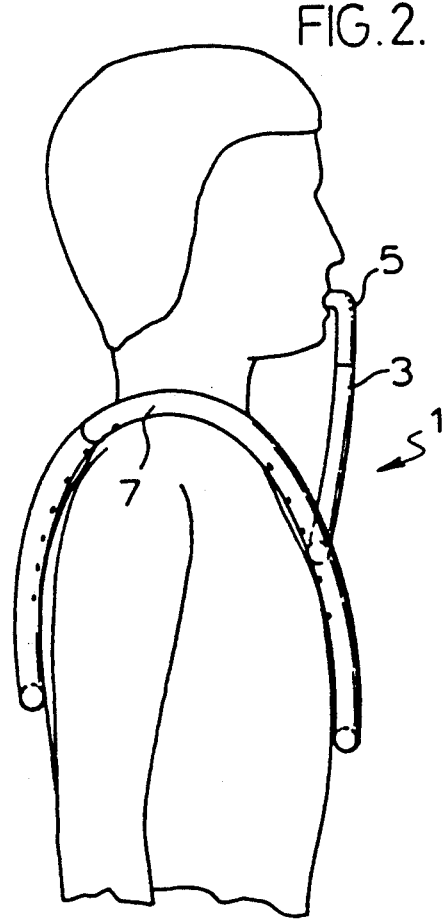
FIG. 2 is a side view of the individual wearing the body warming device of FIG. 1 with the overcoat removed.

As will be seen in FIGS. 1 and 2 the device has a tubular vest like construction with the tubes forming the vest having a relatively soft pliable construction enabling a comfortable shaped fitting beneath the overcoat. Once the device is properly positioned one breathes through mouth piece 5 into tube 3 with the relatively warm breath or air going through manifold 9 to the chest and back portions of the body fitting member. The relatively warm air is then dispersed through exhaust port forming holes 8 providing a warming or insulating layer beneath the overcoat effective on even the coldest of days. In the event that the device is not needed one simple removes the mouth piece from his or her mouth and bends the breathing tube beneath the overcoat where it is out of the way without having to actually remove the device should it be required for further use.

As a natural occurance, the air breathed into the device carries moisture with it. Most of this moisture condenses out of the breathed air when it contacts the inside of the device and therefore is not carried with the warm air passing out through the small holes 8 which would otherwise dampen or wet the users clothing.

Holes 8 are sufficiently small such that the moisture condensed within the device flows along the interior of the tubes forming the chest and back fitting portions to the bottom of the device. Note that the lower part of chest fitting portion 11 includes a non-perforated region 15 while the lower part of back fitting portion 13 includes a non-perforated region 19. These non-perforated regions extend 4 to 5 inches up from the bottom of the device.

Provided at the extreme bottom of the chest fitting portion 11 is a U-shaped non-perforated water trap 17 while cap like water traps 21 are provided at the bottom end of the back fitting portion 13. Each of these traps is held in position by a friction fit to the device. The moisture flowing down the device collects in and above the water traps, i.e. also in the non-perforated regions 15 and 19 of the device, with the water traps being removable to drain the water from the device when needed. It is quite surprising how quickly the water can build up to a depth of 2 to 3 inches within a period of 4 to 6 hours use of the device. Again, without the water traps this water would go directly onto the clothing of the user which quickly cools and more than takes away from the heating benefits provided by the device.

Although various preferred embodiments of the invention have been described herein in detail it will be appreciated by those skilled in the art that variations may be made thereto without departing from the spirit of the invention or the scope of the appended claims.

THE EMBODIMENTS OF THE INVENTION IN WHICH AN EXCLUSIVE PROPERTY OR PRIVILEGE IS CLAIMED ARE DEFINED AS FOLLOWS:

1. A portable body warming device comprising a body fitting member and a mouth insert solid walled breath exhale tube extending to said body fitting member, said body fitting member being worn under an overcoat, said body fitting member receiving relatively warm air breathed through said mouth insert and into said tube and comprising a plurality of downwardly extending tubes having an upper wall region with a plurality of small ports for dispersing exhaled breath from said device beneath the overcoat, said downwardly extending tubes having a closed lower end region free of said ports with removable water trap means being provided at said lower end region for collecting and selectively dispensing moisture condensed within said device, said downwardly extending tubes draining any such moisture directly to said lower end region of said device for later disposal.

2. A body warming device as claimed in claim 1 wherein said body fitting member has a tubular vest-like construction including both chest and back fitting portions each comprising downwardly extending tubes having a perforated wall upper region and a closed wall bottom region covered by a bottom end removable cap.

3. A body warming device as claimed in claim 2 including a solid wall manifold portion to both said chest and back fitting portions from said breath exhale tube.

4. A portable body warming device comprising a vest-like structure formed by forward and rearward downwardly extending tubes, a mouth insert breath exhale tube, and a transverse manifold tube between said breath exhale tube and said downwardly extending tubes, said breath exhale tube and said manifold tube having a solid wall construction, said downwardly extending tubes having breath exhaust ports along an upper region thereof with a closed bottom region for collecting and later dispensing of moisture condensed within said device, said bottom region being provided with a removable cap for selectively draining any such moisture from said device.

* * * * *